United States Patent
Gaffey et al.

(12)

(10) Patent No.: US 10,850,248 B2
(45) Date of Patent: Dec. 1, 2020

(54) CHLORINE DIOXIDE SOLUTION GENERATING APPARATUS

(71) Applicant: GAFFEY TECHNICAL SERVICES LIMITED, Accrington (GB)

(72) Inventors: Philip Gaffey, Accrington (GB); Maxwell Cole, Accrington (GB)

( * ) Notice: Subject to any disclaimer, the term of this patent is extended or adjusted under 35 U.S.C. 154(b) by 0 days.

(21) Appl. No.: 16/315,715

(22) PCT Filed: Jul. 7, 2017

(86) PCT No.: PCT/GB2017/000103
§ 371 (c)(1),
(2) Date: Jan. 7, 2019

(87) PCT Pub. No.: WO2018/011532
PCT Pub. Date: Jan. 18, 2018

(65) Prior Publication Data
US 2019/0381472 A1    Dec. 19, 2019

(30) Foreign Application Priority Data
Jul. 12, 2016    (GB) .................................. 1612077.6

(51) Int. Cl.
*B01J 14/00*    (2006.01)
*B01J 7/02*    (2006.01)
(Continued)

(52) U.S. Cl.
CPC ................. *B01J 14/00* (2013.01); *A61L 2/18* (2013.01); *A61L 2/24* (2013.01); *B01J 7/02* (2013.01);
(Continued)

(58) Field of Classification Search
CPC . B01J 7/02; B01J 14/00; B01J 19/0033; B01J 2219/00164; B01J 2219/00186;
(Continued)

(56) References Cited

U.S. PATENT DOCUMENTS 4,886,653 A * 12/1989 Gasper .................. C01B 11/025
423/478
5,204,081 A    4/1993 Mason et al.
(Continued)

FOREIGN PATENT DOCUMENTS

WO    2003/000586 A1    3/2003

OTHER PUBLICATIONS

International Search Report for PCT/GB2017/000103.
International Preliminary Report on Patentability for PPCT/GB2017/000103.

*Primary Examiner* — Lessanework Seifu
(74) *Attorney, Agent, or Firm* — Egbert Law Offices, PLLC (57) ABSTRACT

A chlorine dioxide solution generating apparatus is provided for use primarily in water treatment. The apparatus has a reaction chamber supplied with metered quantities of an acidic solution and a chlorite or chlorate solution whereby a reservoir of a chlorine dioxide solution is generated and retained within the reaction chamber. A conduit is provided along which a pressurized flow of a motive fluid is fed and with which the interior of the reaction chamber communicates via a dip tube. A venturi is located in the conduit adjacent an outlet from the dip tube whereby suction is applied to the reaction chamber by the pressurized flow of motive fluid. The suction draws chlorine dioxide solution from the reservoir whereby it is entrained into the flow of motive fluid. A controller is provided to control flow of motive fluid and metering of the supply of the solutions to the reaction chamber.

15 Claims, 4 Drawing Sheets

(51) Int. Cl.
*C01B 11/02* (2006.01)
*A61L 2/18* (2006.01)
*A61L 2/24* (2006.01)
*B01J 19/00* (2006.01)
*C02F 1/76* (2006.01)

(52) U.S. Cl.
CPC ......... *B01J 19/0033* (2013.01); *C01B 11/024* (2013.01); *A61L 2202/11* (2013.01); *A61L 2202/14* (2013.01); *B01J 2219/00164* (2013.01); *B01J 2219/00186* (2013.01); *C02F 1/76* (2013.01); *C02F 2303/04* (2013.01)

(58) Field of Classification Search
CPC ... C01B 11/022; C01B 11/023; C01B 11/024; C02F 1/76
See application file for complete search history.

(56) References Cited

U.S. PATENT DOCUMENTS

| | | | |
|---|---|---|---|
| 6,468,479 B1 | 10/2002 | Mason et al. | |
| 8,784,733 B2 * | 7/2014 | Alarid | C01B 7/01 |
| | | | 204/194 |
| 2003/0118503 A1 | 6/2003 | Pu et al. | |
| 2005/0244328 A1 * | 11/2005 | Schmitz | C02F 1/763 |
| | | | 423/477 |
| 2011/0168608 A1 | 7/2011 | Gaffey | |
| 2017/0225977 A1 * | 8/2017 | Cole | C25B 15/02 |

* cited by examiner

Fig. 1
(Part 1 of 2)

Fig. 1
(Part 2 of 2)

CHLORINE DIOXIDE SOLUTION GENERATING APPARATUS

The present invention relates to a chlorine dioxide solution generating apparatus for use primarily in the supply of the solution for water treatment and, in particular, to such an apparatus for use on site in the disinfection of water supplies.

Chlorine dioxide is used in water treatment as a disinfectant primarily for eliminating water-borne pathogens such as *Legionella* bacteria and for preventing the development of biofilms in water storage tanks. It is therefore widely used in industrial applications for process water, for example as washing water in the food industry, and for treating water supplies to large buildings such as office blocks, hospitals and hotels where a water supply is often provided via large header tanks and where air conditioning systems have cooling towers, both of which are known breeding grounds for harmful pathogens.

One of the most important qualities of chlorine dioxide is its high water solubility, especially in cold water, and it is effective even at low concentrations. It does not hydrolyse when it enters water and remains as a dissolved gas in solution. However, chlorine dioxide is a compound that can decompose extremely violently when separated from diluting substances. As a result, preparation methods that involve the production of solutions of it without going through a gas-phase stage are often preferred. Such methods are generally used for its generation for water treatment as the solution produced can then be dosed directly into a water supply. However, it is essential that the chlorine dioxide solutions are handled in a safe manner to retain the chlorine dioxide in solution as should the compound come out of solution it can explosively decompose into chlorine and oxygen. It is for this reason that chlorine dioxide solutions are produced in small batches on site because such solutions cannot be stored for lengthy periods as they are relatively unstable and deteriorate quickly. This not only adds to the risk of explosions occurring but also means that the dosing solution rapidly loses its disinfecting capability.

Conventionally, a chlorine dioxide generating apparatus comprises a reaction chamber in which either an aqueous sodium chlorite solution or an aqueous sodium chlorate solution is mixed with a dilute acid such as hydrochloric acid to produce an aqueous salt and chlorine dioxide solution. Usually, for water treatment an aqueous sodium chlorite solution is mixed with a dilute hydrochloric acid solution in the reaction chamber. The concentration of the chlorine dioxide solution produced is typically between 1% and 5% by volume, as required, and is then further diluted into a motive water stream which is added to the process water or water supply on site. The acidic and sodium chlorite solutions are pumped into the reaction chamber using calibrated dosing pumps. Usually it takes around 15 minutes to produce a chlorine dioxide solution of the required concentration. This chlorine dioxide solution is then either dosed directly from this tank into the process water or water supply or is pumped into a solution storage tank. Hence, the generating apparatus may operate on a batch basis wherein the level of the chlorine dioxide solution in the tank is controlled, a predetermined low level turning on the generation process at a fixed rate. The tank then fills up and stops at a predetermined high level. Metering pumps dose the chlorine dioxide solution from the storage tank into the water to be treated. Alternatively, the generating apparatus may operate on a continuous basis with the chlorine dioxide solution produced in the reaction chamber being injected directly into the process water or water supply at a controlled rate, which is matched by the rate of production in the reaction chamber. The dosing amounts required typically depend upon local authority regulations and the application.

One of the main disadvantages of such conventional systems is that the reaction chamber operates under pressure and is usually designed to withstand pressures up to 15 bar. Potentially, this can cause several problems. First, if the apparatus fails, leakage of dangerous chemicals can occur. It also means that all of the connections between the various parts of the apparatus must be provided with adequate seals, which are themselves open to failure. Second, should the dosing pumps malfunction, which they are prone to do with age, the dosing chemicals may be overdosed to the reaction chamber, which can result in a dangerous build-up of chlorine dioxide gas in the chamber or in an incorrect dosage of the water to be treated, in particular resulting in a surfeit of the dosing acid being added to the water.

An object of the present invention is to provide a chlorine dioxide solution generating apparatus that overcome or substantially mitigates the aforementioned problems.

According to the present invention there is provided chlorine dioxide solution generating apparatus comprising a reaction chamber that is supplied with metered quantities of an acidic solution and a chlorite or chlorate solution from separate sources whereby a reservoir of a chlorine dioxide solution is generated and retained within the reaction chamber;

a conduit along which a pressurized flow of a motive fluid is fed and with which the interior of the reaction chamber communicates via a dip tube;

a venturi located in the conduit adjacent an outlet from the dip tube whereby suction is applied to the interior of the reaction chamber by the pressurized flow of motive fluid to draw chlorine dioxide solution from the reservoir whereby it is entrained into the flow of motive fluid in the conduit; and a controller adapted to control the flow of motive fluid along the conduit and the metering of the supply of said quantities of the acidic solution and the chlorite or chlorate solution to said reaction chamber.

Preferably, the metered quantities of acid and chlorite or chlorate solutions are supplied to the reaction chamber via respective first and second supply pipes that each incorporate a volumetric flow meter and a valve, the opening and closing of the valve being controlled by the controller dependent on the volume of solution that flows through and is measured by the volumetric flow meter.

Preferably also, the conduit is fed with the motive fluid from a pressurized supply of liquid to be disinfected by the chlorine dioxide solution.

Preferably also, the pressurized flow of the motive fluid is metered and controlled by a third volumetric flow meter and a third valve the opening and closing of which is controlled by the controller.

Other preferred but non-essential features of the various aspects of the present invention are described in the dependent claims appended hereto.

The present invention will now be described by way of example with reference to the accompanying drawings, in which:—

Figure 1:
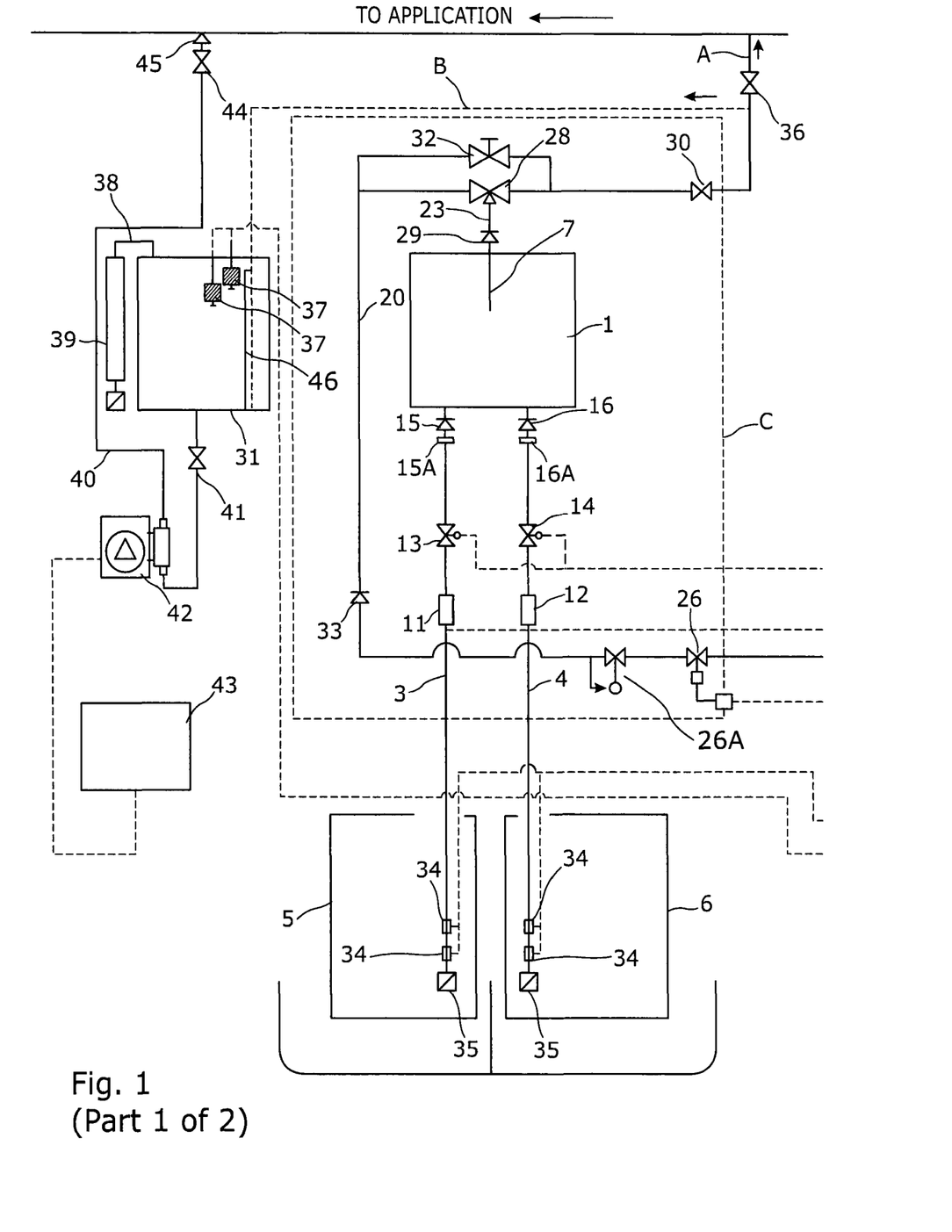
FIG. 1 is a diagram showing the general arrangement of a chlorine dioxide solution generation apparatus according to the present invention.

With reference to the drawings, a chlorine dioxide solution generation apparatus comprises a reaction chamber 1 in which a reservoir 2 of a chlorine dioxide solution is formed by a chemical reaction between metered quantities of an acidic solution and a chlorite or chlorate solution that are supplied to the reaction chamber 1 via respective first and second supply pipes 3 and 4 from tanks 5 and 6. As is described below, these solutions are drawn into the reaction chamber 1 by negative pressure in the chamber 1 that is created when quantities of the chlorine dioxide solution from the reservoir 2 are sucked out through a dip tube 7 which is inserted into the chamber 1, its inlet 8 being located at the upper level 9 of the reservoir 2. The quantities of the solutions supplied to the chamber 1 are controlled by an electronic, preferably programmable controller 10 that is operationally linked to first and second volumetric flow meters 11 and 12 and first and second valves 13 and 14, typically solenoid valves, which are respectively located in the first and second supply pipes 3 and 4. Downstream of the valves 13 and 14 in the supply pipes 3 and 4 are first and second non-return valves 15 and 16 respectively that may include restrictors 15A and 16A, if necessary, dependent on the flow conditions in the pipes 3 and 4.

Figure 2:
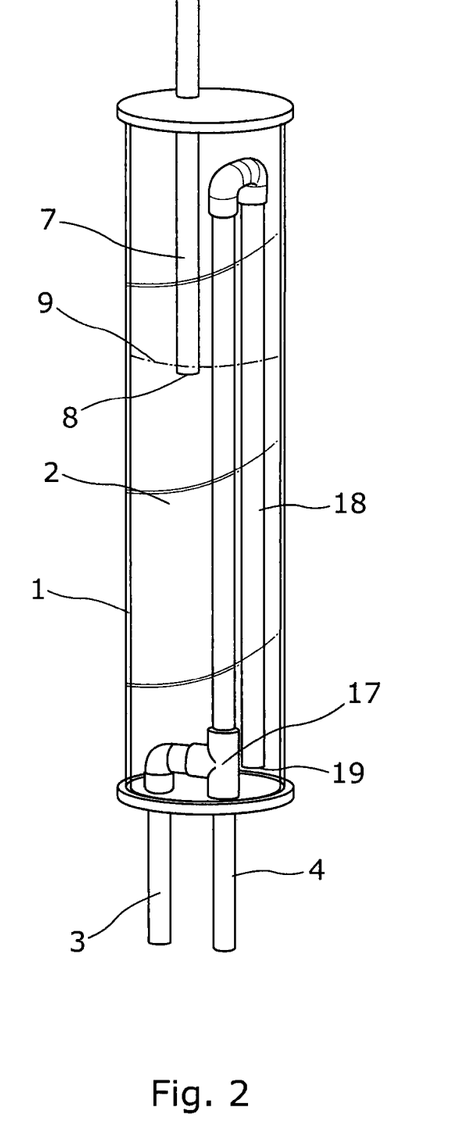
FIG. 2 is a perspective schematic view of a set-up within a reaction chamber forming part of the apparatus shown in FIG. 1.

A first set-up within the reaction chamber 1 is shown in FIG. 2. Here, the outlets from the supply pipes 3, 4 are merged by means of a mixing tee 17 that is connected to a blending column 18 of inverted U-shape. The mixing tee 17 and the blending column 18 ensure that the solutions from the tanks 5, 6 are blended and well mixed prior to egressing from the column 18 via an outlet 19 that is located close to the base of the reaction chamber 1 and below the lower level of the dip tube 7. Usually, it takes around 15 minutes to achieve the maximum production of chlorine dioxide from a mixture of an aqueous sodium chlorite solution and a dilute hydrochloric acid solution. Hence, the requirement for a sufficient reservoir 2 in the reaction chamber 1 to ensure a constant supply of a suitable strength chlorine dioxide solution and also good mixing of the reacting solutions as they flow into the chamber 1. For reasons that are explained below, the level of the inlet 8 into the dip tube 7 is always located at the upper level 9 of the reservoir 2 and therefore the height of the inlet 8 above the base of the reaction chamber 1 determines the size of the reservoir 2, that is the quantity of solution retained within the reaction chamber 1. This quantity should be an appropriate quantity dependent on the rate at which it will be used for disinfection purposes, which in turn is dependent on the application, and the time taken for the solutions from the tanks 5 and 6 to react fully. As the reaction time is typically of the order of 15 minutes, it is necessary for the dwell time of the solutions in the reaction chamber 1 to be this long. Using this data and dependent on the application the optimum size of the reservoir 2 can be predetermined by a person skilled in the art. In turn, this governs the position of the inlet 8 of the dip tube 7 in the reaction chamber 1.

An advantage of this set-up is that the size of the reaction chamber 1 is not dependent on the required size of the reservoir 2 provided that it can be accommodated in the chamber 1. Instead, the level of the inlet 8 into the dip tube 7 is the critical factor that determines the size of the reservoir 2 and this level can be varied to suit the application. In some embodiments, the dip tube 7 is fitted to the reaction chamber 1 in such a way that the level of its inlet 8 can be adjusted on site as required and only one size of reaction chamber 1 needs to be supplied as it can be used for a wide range of applications where the rate of production of chlorine dioxide solution may vary widely.

Figure 3:
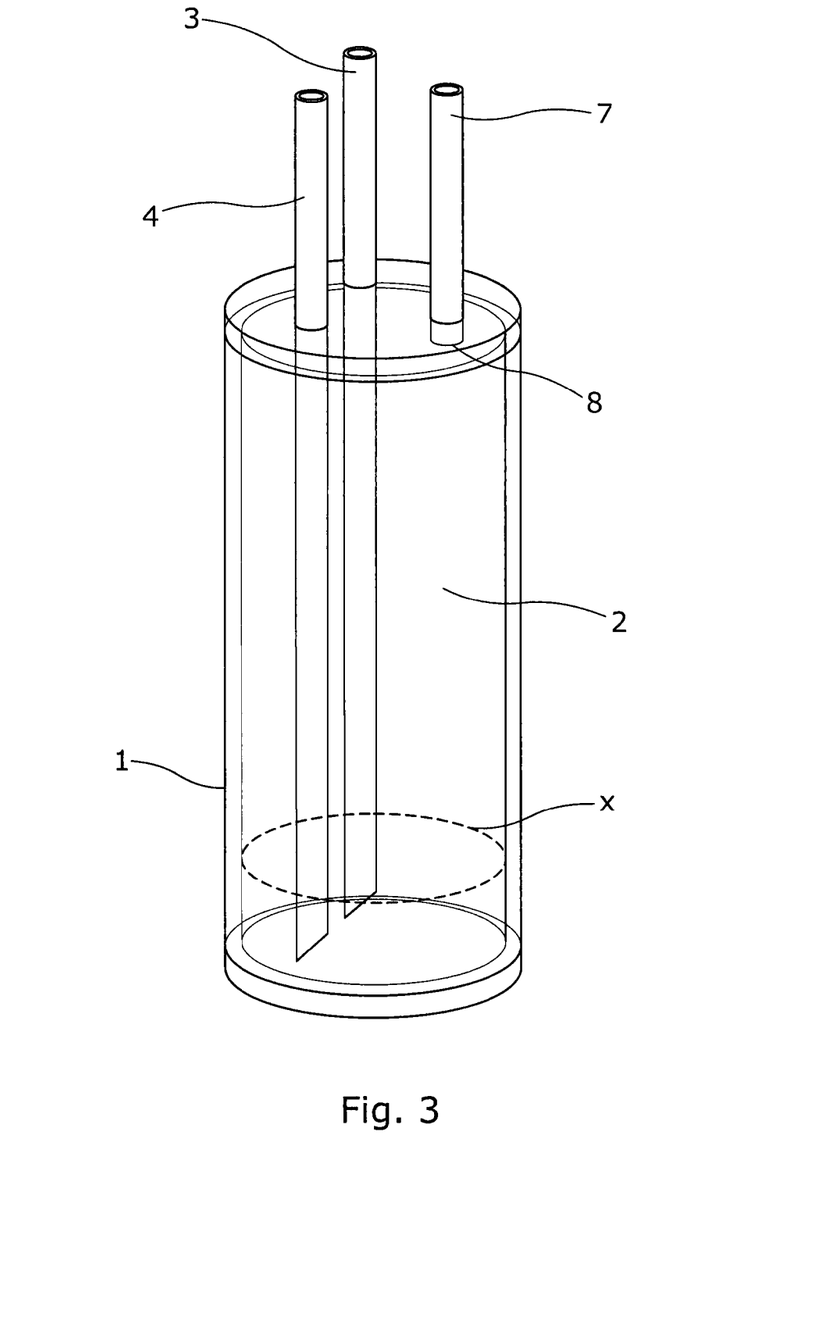
FIG. 3 is a view similar to FIG. 2 but of a modified set up of reaction chamber for forming part of the apparatus shown in FIG. 1.

However, such a set-up has some disadvantages, in particular the requirement to create negative pressure within the reaction chamber 1 when air is present above the upper level of the reservoir. Also, leakage from the reservoir 1 is apt to occur eventually around inlets for the supply pipes 3, 4 that pass through the bottom of the reaction chamber 1. Hence, an alternative set-up for the chamber 1 is shown in FIG. 3. Here, the supply pipes 3, 4 enter the top of the reaction chamber 1 and terminate just above the base of the chamber 1 in a lower region that in use will contain an inert aggregate, such as ceramic beads, up to a predetermined level marked X. This inert aggregate facilitates blending of the two reagents. Preferably, the ends of the supply pipes 3, 4 are chamfered to prevent their hitting the bottom of the chamber 1 and becoming blocked. In this arrangement the size of the reaction chamber 1 is dependent on the required size of the reservoir 2 and is factory set as it is a requirement for the chamber 1 to be virtually always full of the chlorine dioxide solution. Hence, the inlet 8 of the dip tube 7 is very close to the top of the reaction chamber 1.

In both set-ups chlorine dioxide solution is drawn from the reservoir 1 through the dip tube 7, which is connected to a conduit 20 that is fed with a pressurized flow of a motive fluid as an offshoot from a pressurized supply pipe 21, which may be a water mains supply or similar pressurized supply of liquid to be disinfected by the chlorine dioxide solution. An isolating valve 22 is provided in the conduit 20 to enable the apparatus to be isolated from the mains supply pipe 21 if necessary. Between the valve 22 and an outlet pipe 23 from the dip tube 7 is a pressure regulating valve 24A, a third volumetric flow meter 25, a valve 26, which is typically a solenoid valve, and a pressure regulating valve 26A that provides stable flow characteristics along the conduit 20. The valves 24A, 26 and 26A and the flow meter 25 are all operationally linked to the controller 10. In addition, a fourth volumetric flow meter 27 is located in the mains supply pipe 21 upstream of the conduit 20 and is operationally connected to the controller 10.

In some embodiments where the pressure in the mains supply pipe 21 is low, the pressure regulating valve 24A may be replaced by a circulating pump 24B, the operation of which is also controlled by the controller 10. Both the valve 24A and the pump 24B are shown in parallel in FIG. 1 but in practice only one or the other of them would be used.

A venturi 28 is located in the conduit 20 adjacent the outlet from then outlet pipe 23 from the dip tube 7. The motive flow of pressurized liquid through the venturi 28 over the end of the outlet pipe 23 applies suction to the interior of the dip tube 7 and therefore to the interior of the reaction chamber 1. This draws chlorine dioxide solution from the reservoir 2, through a non-return valve 29 and into the venturi 28 where it is entrained into the flow of motive fluid in the conduit 20 and conducted via a second isolating valve 30 either back to the mains supply pipe 21 through a pipe A or to a batch storage tank 31 along a pipe B dependent on the application. The pipe B terminates inside the batch storage tank 31 at a low level to ensure that there is always a liquid/gas trap between the batch storage tank 31 and the chamber 1 to retain chlorine dioxide gas within the chamber 1. The prevention of the escape of chlorine dioxide gas to the batch storage tank 31 and to atmosphere improves the efficiency of the reaction process by retaining the gas in the chamber 1 so that it can be homogenised in the venturi 28 during any subsequent batch sequences.

Optionally, the operation of the venturi 28 may be controlled by the setting of by-pass valve 32 that is located in parallel with the venturi 28 in the conduit 20. In addition, immediately upstream of the venturi 28 in the conduit 20 is a non-return valve 33.

The levels of the solutions in the supply tanks 5 and 6 are monitored by float switches 34 which are linked to the controller 10. In addition, the ends of the supply pipes 3 and 4 within the tanks 5 and 6 are connected to non-return foot valves 35, the inlets of which are covered by fine mesh to prevent contaminating particles of other debris from being drawn into the apparatus from the tanks 5, 6.

The non-return valves 15, 16 and 29 control the flow of solutions into and out of the reaction chamber 1 and it is important that they operate efficiently. For this reason, these valves 15, 16, 29 are preferably sprung non-return valves with titanium springs being used so that their operation is unaffected by the corrosive and oxidative nature of the solutions passing through them.

In those embodiments wherein the chlorine dioxide solution from the reaction chamber 1 is injected directly into the mains water supply pipe 21 along pipe A, that is the apparatus will operate in a "continuous mode", a further isolating valve 36 may be provided downstream of the valve 30 so that a unit C, comprising the components within the rectangle shown in dashed lines in FIG. 1, may be completely isolated from the mains water supply. In other embodiments wherein the chlorine dioxide solution from the reaction chamber 1 is stored in a batch storage tank 31, that is the apparatus will operate in a "batch mode", one or more high and low level sensors 37 may be provided in the tank 30 and linked to the controller 10. The sensors 37 may be used by the controller 10 to start and stop operation of the apparatus to ensure that there is always an adequate supply of chlorine dioxide solution in the tank 31.

The unit C along with the controller 10 may be supplied separately from the other components of the apparatus described above as it is suitable for retro-fitment to an existing water supply installation.

In the embodiments that use a batch storage tank 31, it will be appreciated that the storage tank 30 may retain the chlorine dioxide solution for some time and consequently it is possible for the chlorine dioxide start to come out of solution and create a pressure build-up within the tank 31. This would be a dangerous, potentially explosive hazard. To prevent this from happening, the tank 31 is maintained at atmospheric pressure via vent 38 in which is located a scrubber 39 that removes the chlorine dioxide from the gas passing through it.

The chlorine dioxide solution in the tank 31 is dosed into mains supply pipe 21 through a pipe 40 via an isolating valve 41 and dosing pump 42, the operation of which is controlled by a pump controller 43. Alternatively, the dosing pump 42 could be connected to the controller 10 and the separate pump controller 43 dispensed with. A further isolating valve 44 and non-return valve 45 are preferably also included in the pipe 40 downstream of the dosing pump 42. Also a weir 46 may be provided in the tank 31, isolating the inlet from pipe B from the bulk of the chlorine dioxide solution stored in the tank 31 from a supply is drawn via the pipe 40.

The controller 10 preferably comprises a dedicated, programmable device that may include a remote control option 47, for example via the Internet or Wi-Fi. For safety, the controller 10 also incorporates an emergency stop button 48 that is set up to cause the immediate cessation of chlorine dioxide generation by the apparatus and the closure of the valves 13, 14 and the valve 24A or pump 24B.

In use, all of the isolating valves 22, 30, 36, 41 and 44 are open and, the controller 10 is powered up. After running through a series of checks to ensure that alarm conditions can be safely monitored the controller 10 commences operation of the apparatus. First, in the case that the apparatus is newly commissioned the reaction chamber 1 will be empty so that the reservoir 2 must first be created by filling the reaction chamber 1 with the required volume of chlorine dioxide solution. This is a known predetermined quantity, as indicated above, that has already been catered for by the position of the dip tube 7 in the reaction chamber 1. Hence, the controller 10 opens the motive fluid flow valve 26 and the valves 13 and 14. The valve 26 is opened for a predetermined volume as measured by the third flow sensor 25 prior to the valve 13 and in turn the valve 14 being opened sequentially, to establish and maintain a controlled vacuum in the outlet pipe 23. The valve 26 is retained open sufficient for the predetermined volume as measured by the flow sensor 25 to flow through after the valves 13 and 14 close, which is governed by the volume passing through the flow sensors 11 & 12. This is in order to deliver remaining water required to maintain a correct ratio of water and chlorine dioxide solution entering the batch tank 31 and also to act as a water purge to remove any remaining chlorine dioxide solution from the venturi 28 and send it to the batch tank 31.

By controlling the total batch water volume using the flow sensor 25 in relation to the volume of chemical reagents passing through the flow sensors 11 and 12, the controller 10 can be programmed to produce a predetermined strength of chlorine dioxide solution that is delivered to the batch tank 31 by controlling operation of the regulating valves 11, 12 and 26.

The motive flow through the venturi 28 sucks air out of the reaction chamber 1, which in turn sucks in the solutions from the tanks 5 and 6. The quantities of each solution from the tanks 5 and 6 is monitored by the volumetric flow meters 11 and 12 and when each of them has passed the required volume of solution therethrough, the controller 10 closes the relevant valve 13, 14 to ensure that the correct quantity of that solution has entered the reaction chamber 1. Similarly, when the required volume of motive fluid has passed through the volumetric flow meter 25, the valve 26 is also closed. The non-return valves 15 and 16 ensure that the solutions are retained within the reaction chamber 1 and the non-return valve 33 ensures that the motive fluid is retained in the conduit 20.

The efficiency of the venturi 28 and its repeatable performance is governed by its pressurized water stream 20 operating at a predetermined pressure set by the pressure regulating valve 26A and the inherent back pressure downstream that is governed by the height of the weir 46 in the batch tank 31.

The motive fluid which has been used to draw the initial quantity of the solutions into the reaction chamber 1 can either be allowed to flow directly back into the mains flow in pipe 21 via the valves 30 and 36 or to flow into the batch storage tank 31 where it be immediately pumped back into the mains flows in the pipe 21 by the dosing pump 42 in order not to dilute the dosing solution which will subsequently be stored in the tank 31. Once the reaction chamber 1 contains the requisite quantities of the solutions from the tanks 5, 6 then the controller 10 will wait for a reaction time of around 15 minutes for generation of the chlorine dioxide solution in the chamber 1 before initiating a steady state operation of the apparatus. If the apparatus is operating in a batch mode to produce a batch of chlorine dioxide solution in the batch storage tank 31 via pipe B the following sequence is used.

a. The motive fluid flow valve 26 is opened.

b. The acid and chlorite/chlorate valves 13 and 14 are opened sequentially.

c. Once the volumetric flow meters 11, 12 have signalled to the controller that predetermined volumes of the acid solution and the chlorite or chlorate solution have passed through them the controller closes the valves 13, 14,     e. When the volumetric flow meter 25 has signalled to the controller that a correct predetermined volume of motive fluid has passed through it, the controller closes the valve 26.

d. The controller 10 waits for a predetermined cycle time, typically between 1 to 2 minutes, and then repeats the cycle from point a. above.

This sequence of operation produces a concentrated supply of chlorine dioxide solution in the batch storage tank 31, which is subsequently dosed into the mains water supply 21 by the dosing pump 42 under the control of the pump controller 43. The level sensors 37 in the tank 31 allow the controller to stop the aforementioned sequence when the level of solution in the tank 31 is high and to commence it again once the level drops below a predetermined lower level.

It should be appreciated that once the reservoir 2 has been created in the reaction chamber 1, its upper level 9 remains substantially constant because the same quantity of liquid leaves the reaction chamber 1 as is sucked into it by the action of the venturi 28. Should the level of the solutions in the tanks 5, 6 fall to a low level, this is also signalled to the controller to by the float switches 34 and the controller 10 will also act to close the valves 13 and 15 to cease the aforementioned sequence until the tank 5, 6 is replenished or replaced. Also, should either or both of the volumetric flow sensors 11 and 12 detect an abnormal disturbance, for example if air rather than liquid is passing through suggesting that there may be an obstruction in pipes 3, 4 or that the tanks 5, 6 are empty, for more than a predetermined time, typically a few seconds, then the controller 10 will act to close the valves 13, 14 and 26 and to stop operation of the apparatus.

On the other hand, if the apparatus is operating in a continuous mode to inject the chlorine dioxide solution from the reaction chamber 1 directly into the mains water supply pipe 21 via pipe A, then the following sequence may be followed.

a. The motive fluid flow valve 26 is opened.

b. The acid and chlorite/chlorate valves 13 and 14 are opened.

c. Once the volumetric flow meters 11, 12 have signalled to the controller that predetermined volumes of the acid solution and the chlorite or chlorate solution have passed through them the controller closes the valves 13, 14,     d. When the volumetric flow meter 25 has signalled to the controller that a correct predetermined volume of motive fluid has passed through it, the controller closes the valve 26.

e. The controller 10 waits for a predetermined cycle time, and then repeats the cycle from point b. above.

In this mode, typically the volume of the reservoir 2 will be larger and the predetermined cycle time much shorter than in the batch mode. The motive fluid flow along the conduit 30 will be continuous so that it is constantly entraining chlorine dioxide solution from the reaction chamber 1. However, the quantity of liquid sucked out of the chamber 1 will be matched by the quantities of liquid flowing in through the pipes 3, 4 as soon as the valves 13, 14 open owing to the negative pressure build up within the chamber 1. However, it is necessary to program the controller 10 such that the volumes of liquid passing through the volumetric flow meters 11, 12 can match the quantity being drawn off through the dip tube 7 so that the upper level 9 of the reservoir remains substantially constant.

The volumetric flow meter 25 is an important part of the apparatus as it controls the volume of motive fluid passing along conduit 20 and therefore the dilution of the solution being produced by the apparatus. If for any reason the flow of motive fluid is interrupted or for any reason the correct volume of motive fluid passing through the flow meter 25 in a given time cannot be maintained or is too high, then the controller 10 will act to close the valves 13, 14 and 26, in order to stop operation of the apparatus. The controller 10 will also signal an alarm so that the problem can be investigated. The volumetric flow meter 25 therefore acts as a "watchdog", monitoring that the apparatus is operating correctly.

The apparatus according to the invention has several advantages over conventional apparatus, as follows.

1. The quantities of acid solution and the chlorite or chlorate solution supplied to the reaction chamber 1 are measured by the volumetric flow meters 11 and 12, which accurately measure the volume of liquid passing through them, rather than via dosing pumps. This is a significantly more precise way of measuring small quantities of liquid as dosing pumps tend to become less accurate over time as their constituent parts wear.

2. Unlike conventional apparatus wherein the reaction chamber 1 operates under pressure, in the present invention the reaction chamber 1 is open to atmosphere or subject to negative pressure. This means that the chamber 1 is less likely to leak and if a seal fails, the chlorine dioxide solution is less likely to be expelled from the chamber 1.

3. As the reaction chamber 1 is not subject to high pressures it can be made of a durable plastics material, such as polyvinylidene fluoride, or polyvinylidene difluoride (PVDF), as can much of the rest of the apparatus. This makes the apparatus less expensive to produce and increases the life of the apparatus, which otherwise tends to suffer from degradation by the acidic and oxidative solutions used.

4. In order for the apparatus to produce the chlorine dioxide solution in the reaction chamber 1 there has to be a pressurized flow of motive fluid in the conduit 20. Hence, should the flow of fluid in the mains supply pipe 21 be interrupted for any reason, such as a burst pipe, then the production of chlorine dioxide solution in the reaction chamber 1 will cease. This is safer than conventional arrangements wherein the production of the chlorine dioxide solution is unaffected by problems in the mains water supply, which can lead to an unacceptable overdosing of the supply when reconnected.

5. After initial set-up, the reaction chamber 1 always contains the correct solution and cannot be contaminated by an over-supply of either the acid solution or the chlorite or chlorate solution.

The invention claimed is:

1. A chlorine dioxide solution generating apparatus comprising:

a reaction chamber that is supplied with metered quantities of an acidic solution and a chlorite or chlorate solution from separate sources whereby a reservoir of a chlorine dioxide solution is generated and retained within said reaction chamber;

a plurality of supply pipes for respectively supplying the metered quantities of the acidic solution and the chlorite or chlorate solution to the reaction chamber, said plurality of supply pipes entering a top of said reaction chamber and terminating in a lower region of the reaction chamber;

an inert aggregate contained within the lower region of said reaction chamber;

a conduit along which a pressurized flow of a motive fluid is fed and with which an interior of said reaction chamber communicates via a dip tube;

a venturi positioned in the conduit adjacent an outlet from the dip tube whereby suction is applied to the interior of said reaction chamber by the pressurized flow of the motive fluid to draw the chlorine dioxide solution from the reservoir whereby the chlorine dioxide solution is entrained into the pressurized flow of the motive fluid in said conduit; and a controller adapted to control the flow of motive fluid along said conduit and the metering of the supply of the metered quantities of the acidic solution and the chlorite or chlorate solution to said reaction chamber.

2. The chlorine dioxide solution generating of apparatus claim 1, wherein the metered quantities of acid and chlorite or chlorate solutions are supplied to the reaction chamber via respective first and second supply pipes that each has a volumetric flow meter and a valve, an opening and a closing of the valve being controlled by said controller dependent on a volume of solution that flows through and is measured by the volumetric flow meter.

3. The chlorine dioxide solution generating of claim 2, wherein first and second non-return valves are respectively located in the first and second supply pipes downstream of the volumetric flow meter and the valve, the volumetric flow meter comprising a first volumetric flow meter and a second volumetric flow meter, the valve comprising a first valve and a second valve.

4. The chlorine dioxide solution generating of claim 1, wherein said conduit is fed with the motive fluid from a pressurized supply of liquid.

5. The chlorine dioxide solution generating of claim 3, wherein the pressurized flow of the motive fluid is metered and controlled by a third volumetric flow meter and a third valve, an opening and a closing of the third valve being controlled by said controller.

6. The chlorine dioxide solution generating of claim 5, wherein a non-return valve is positioned in said conduit upstream of said venturi and downstream of the third volumetric flow meter and the third valve.

7. The chlorine dioxide solution generating of claim 6, wherein another non-return valve is positioned in the outlet from the dip tube so as to prevent a backflow of the chlorine dioxide solution into said reaction chamber.

8. The chlorine dioxide solution generating of claim 1, wherein a size of the reservoir corresponds to a level of an inlet of the dip tube in the reaction chamber.

9. The chlorine dioxide solution generating of claim 1, wherein the metered quantities of the acidic solution and the chlorite or chlorate solution are mixed and blended together in a blending column prior to egressing from the blending column into said reaction chamber.

10. The chlorine dioxide solution generating of claim 9, wherein the blending column is positioned within said reaction chamber, the blending column having an outlet positioned adjacent a base of said reaction chamber and below a lower level of the dip tube in said reaction chamber.

11. The chlorine dioxide solution generating of claim 1, wherein ends of the plurality of supply pipes are chamfered.

12. The chlorine dioxide solution generating of claim 1, wherein said conduit discharges the motive fluid and the entrained chlorine dioxide solution into a batch storage tank downstream of said venturi.

13. The chlorine dioxide solution generating of claim 12, wherein said conduit terminates at a lower level within the batch storage tank and adapted to create a liquid/gas trap between the batch storage tank and said reaction chamber.

14. The chlorine dioxide solution generating of claim 12, wherein the batch storage tank has level sensors that are linked to said controller whereby the supply of metered quantities of the acidic solution and the chlorite or chlorate solution to the reaction chamber is commenced when a level of liquid in the batch storage tank is low and stopped when the level of liquid in the batch storage tank is high.

15. The chlorine dioxide solution generating of claim 1, further comprising:

a first supply tank containing the acidic solution; and a second supply tank containing the acidic solution, each of said first and second supply tanks having a level sensor linked to said controller, said controller adapted to stop a slow of the metered quantities of the acidic solution and the chlorite or chlorate solution to said reaction chamber when the level sensor senses when a level of the solution in the first and second supply tank is low.

* * * * *